United States Patent
Hester, Jr.

[11] 3,994,940
[45] Nov. 30, 1976

[54] PREPARATION OF 1-(2-(DIMETHYLAMINO)ETHYL)-6-PHENYL-4H-5-TRIAZOLO(4,3-a)(1,4)BENZODIAZEPINES

[75] Inventor: Jackson B. Hester, Jr., Galesburg, Mich.

[73] Assignee: The Upjohn Company, Kalamazoo, Mich.

[22] Filed: Jan. 20, 1975

[21] Appl. No.: 542,388

[52] U.S. Cl.............. 260/308 R; 260/256.4 Q; 260/562 P; 260/570 AB; 424/269
[51] Int. Cl.²........................ C07D 487/04
[58] Field of Search.................. 260/308 R

[56] References Cited

UNITED STATES PATENTS

| | | | |
|---|---|---|---|
| 3,842,090 | 10/1974 | Gall et al. | 260/308 R |
| 3,882,139 | 5/1975 | Gall et al. | 260/308 R |

*Primary Examiner*—Alton D. Rollins
*Attorney, Agent, or Firm*—Hans L. Berneis

[57] ABSTRACT

A process for the production of known compounds of the formula IV

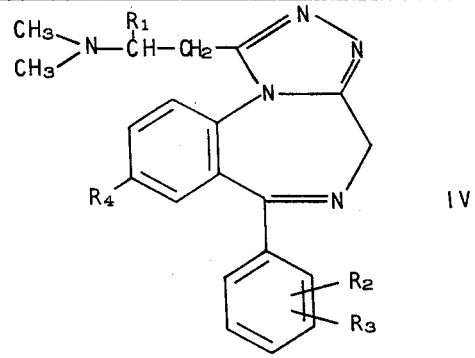

wherein $R_1$ is hydrogen or alkyl of 1 to 3 carbon atoms, inclusive; wherein $R_2$ is hydrogen, chloro, or fluoro; wherein $R_3$ is hydrogen, or fluoro with the proviso that $R_3$ is not fluoro if $R_2$ is chloro; wherein $R_4$ is hydrogen, chloro, fluoro, bromo, nitro, and trifluoromethyl, which comprises: treating a compound of the formula I:

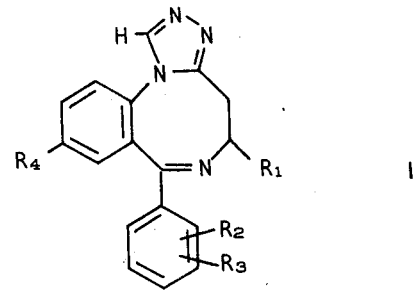

wherein $R_1$, $R_2$, $R_3$, and $R_4$ have the same significance as above, in formic acid solution with aqueous formaldehyde; treating the resulting compound with phthalimide, triphenylphosphine and then diethyl azodicarboxylate to give a compound which when heated with hydrazine, gives compound IV above.

The compounds of formula IV above are known useful antidepressant, tranquilizing, sedative and anti-convulsant agents. The intermediates have also activity in the sedative-tranquilizing area and these compounds can be used in mammals and birds for tranquilization.

5 Claims, No Drawings

PREPARATION OF 1-(2-(DIMETHYLAMINO)ETHYL)-6-PHENYL-4H-5-TRIAZOLO(4,3-a)(1,4)BENZODIAZEPINES

BACKGROUND OF THE INVENTION

Field of the Invention

This invention is directed to a new process for organic compounds and is particularly concerned with a process for 1-[2-(dimethylamino)ethyl]-6-phenyl-4H-s-triazolo[4,3-a][1,4]benzodiazepines and novel intermediates therefor.

The novel compounds and the process of production therefor can be illustratively represented as follows:

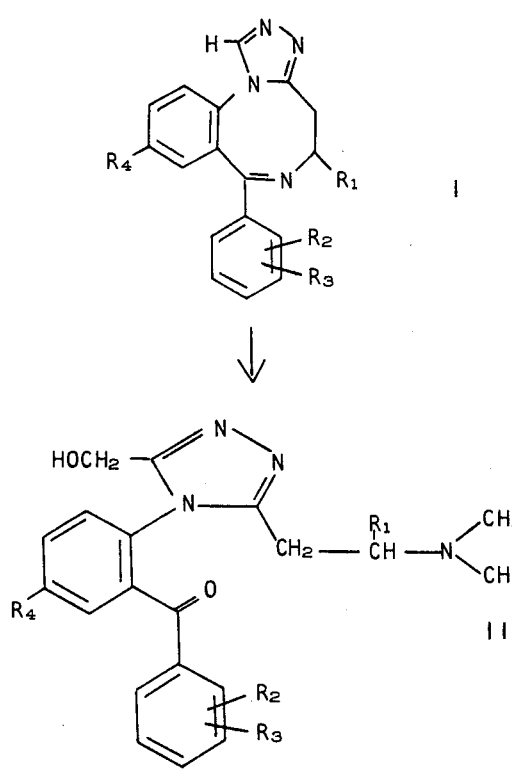

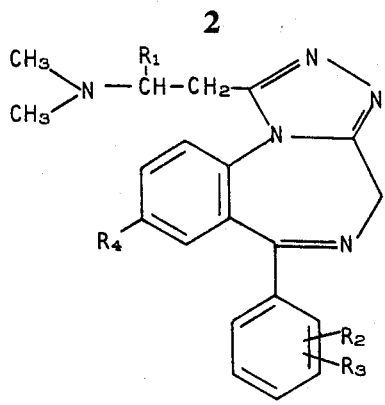

wherein R is hydrogen or alkyl of 1 to 3 carbon atoms, inclusive; wherein R is hydrogen, chloro, or fluoro; wherein $R_3$ is hydrogen or fluoro with the proviso that $R_3$ is not fluoro if $R_2$ is chloro; wherein $R_4$ is hydrogen, fluoro, chloro, bromo, trifluoromethyl, and nitro.

The invention also embraces the pharmacologically acceptable acid addition salts of the new compounds of formulae II and III.

The process of this invention comprises: treating a compound of formula I in formic acid solution with at least 3 equivalents of formaldehyde at reflux temperature to obtain compound II; treating compound II with phthalimide, triphenylphosphine and a proton acceptor such as diethyl azodicarboxylate, in an inert organic solvent, at 0° to 100° C., to give compound III and treating compound III with an acid or a base, with hydrazine preferred, to produce hydrolysis and cyclization and to give product IV above.

DESCRIPTION OF THE PREFERRED EMBODIMENT

Lower alkyl groups of 1 to 3 carbon atoms, inclusive; are exemplified by methyl, ethyl, propyl and isopropyl.

The more desirable products of formula II are of the specific formula IIA:

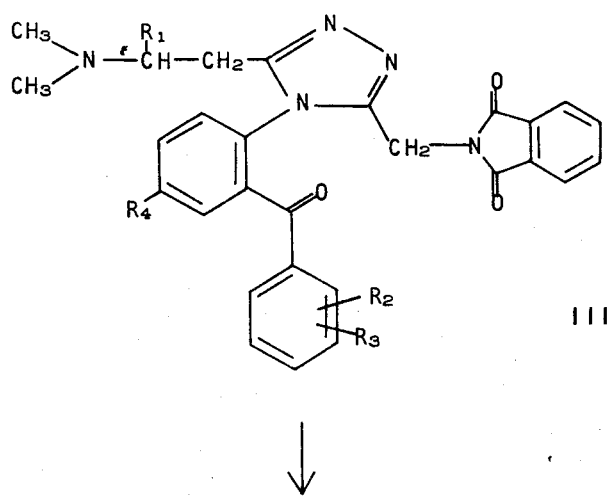

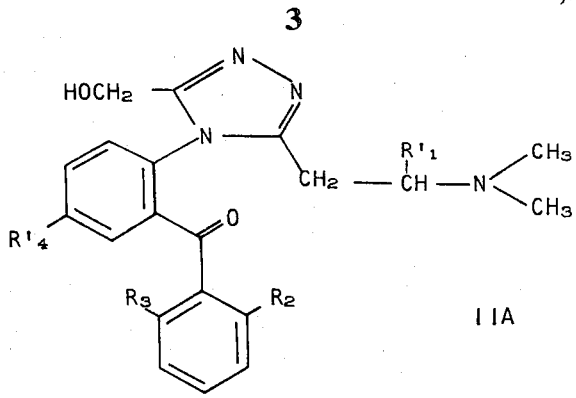

IIA wherein $R'_1$ is hydrogen or methyl; wherein $R_2$ is hydrogen, fluoro, or chloro; wherein $R_3$ is hydrogen or fluoro with the proviso that $R_3$ is not fluoro if $R_2$ is chloro; and wherein $R'_4$ is hydrogen, fluoro, chloro, or trifluoromethyl and the pharmacologically acceptable acid addition salts thereof.

The most desirable products of formula II are of the specific formula IIB:

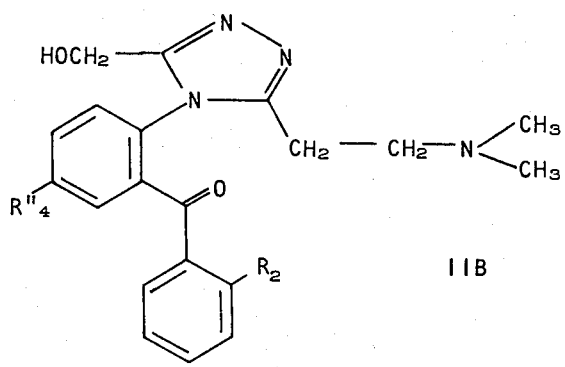

IIB wherein $R_2$ is hydrogen, fluoro, or chloro; and wherein $R''_4$ is hydrogen, fluoro, or chloro, and the pharmacologically acceptable acid addition salts thereof.

The more desirable compounds of formula III are of the specific formula IIIA:

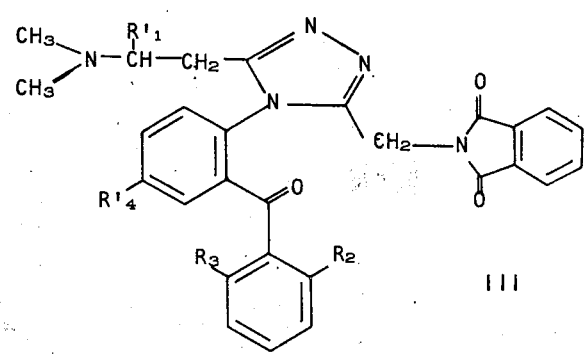

III wherein $R'_1$ is hydrogen or methyl; wherein $R_2$ is hydrogen, fluoro, or chloro; wherein $R_3$ is hydrogen or fluoro with the proviso that $R_3$ is not fluoro if $R_2$ is chloro; and wherein $R'_4$ is hydrogen, fluoro, chloro, or trifluoromethyl and the pharmacologically acceptable acid addition salts thereof.

The most desirable products of formula III are of the specific formula IIIB:

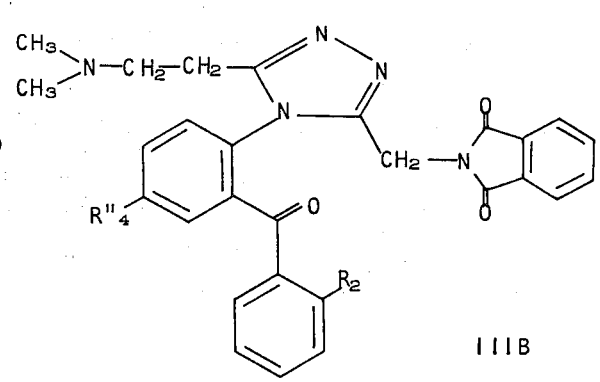

IIIB wherein $R_2$ is hydrogen, fluoro, or chloro; and wherein $R''_4$ is hydrogen, fluoro, or chloro; and the pharmacologically acceptable acid addition salts thereof.

The novel compounds of the formulae II and III (including the preferred species IIA, IIB, IIIA, IIIB) and including acid addition salts thereof have sedative, tranquilizing, and muscle relaxant effects in mammals including man and birds.

The acid addition salts of compounds of formula I, II, and III, contemplated in this invention, are the hydrochlorides, hydrobromides, hydriodides, sulfates, phosphates, cyclohexanesulfamates, methanesulfonates and the like, prepared by reacting a compound of formula I, II or III with an excess of the selected pharmacologically acceptable acid.

Sedative effects of compounds of formula II and III are shown by the following tests in mice:

Chimney test: [Med. Exp. 4, 145 (1961)]: The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of the test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute. The $ED_{50}$ is the dosage at which 50% of the mice remain for more than 1 minute on the pedestal.

Nicotine antaqonism test: Mice in a group of 6 are injected with the test compound. Thirty minutes later the mice including control (untreated) mice are injected with nicotine salicylate (2 mg./kg.). The control mice show overstimulation, i.e., (1) running convulsions followed by (2) tonic extensor fits followed by (3) death. An intraperitoneal dosage of the test compound which protects the mice against (2) and (3) is the $ED_{50}$.

The new compounds II and III are however most useful as intermediates in the production of compounds of the formula IV.

The starting compounds of formula I are obtained as described in the preparations.

In carrying out the process of this invention a selected compound of formula I is reacted with at least 3 mol equivalents, preferably an excess of 5 to 15 mol equivalents, of aqueous formaldehyde in formic acid solution. The formic acid employed is usually 88% formic acid-12% water (as commercially obtainable) and the formaldehyde is conveniently 37% aqueous formaldehyde (formalin). In the preferred embodiment of this invention the reaction is carried out at the reflux temperature of the mixture, about 100° C., during 12 to 24 hours, with 5 to 15 molar equivalents of formalin to 1 molar equivalent of compound I, and in a nitrogen atmosphere. After the reaction is completed the product II is isolated and purified by conventional procedures such as extracting the neutralized reaction mixture with a water-immiscible organic solvent, e.g. chloroform, benzene, ether, and the like, evaporating the extracts, and chromatographing or crystallizing the solids obtained by evaporation.

The thus obtained compound II, in an inert organic solvent, is then treated between 0° to 100° C. with phthalimide, triphenyl phosphine and finally a proton acceptor to give compound III. In the preferred embodiment of this invention this reaction is carried out at about ambient temperatures i.e. 18° to 30° C. under stirring and with a solvent such as tetrahydrofuran, dioxane, diethyl ether, methylene chloride, 1,2-dimethoxyethane and the like. The preferred proton acceptor is diethyl azodicarboxylate. The time of reaction is between 2 to 36 hours. After the reaction is terminated compound III is isolated and purified by conventional means such as extraction, chromatography and crystallization.

Compound III is converted to compound IV by treatment with a base or a mineral acid, in an inert organic solvent, between 25° to 100° C., for a period of 1 to 5 hours. As bases hydrazine or monoalkylamines, such as methylamine, ethylamine or propylamines can be used. As mineral acids hydrochloric or hydrobromic acids are useful. In the preferred embodiment of this invention a lower alkanol e.g. methanol, ethanol 1- or 2-propanol, are used with an excess of preferred base, hydrazine usually as hydrazine hydrate. The reaction is then carried out at the reflux temperature of the mixture during a period of 1 to 6 hours. Thereafter the product IV is isolated by standard procedures, e.g. filtration of the reaction mixture and concentration of the filtrate followed by extraction, chromatography and/or crystallization, often after the product IV is converted to an acid addition salt.

The following preparations and examples are illustrative of the process and products of the present invention, but are not to be construed as limiting.

The starting compounds of formula I are prepared by the following scheme:

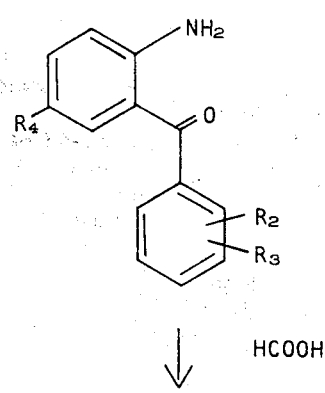

(a)

↓ HCOOH

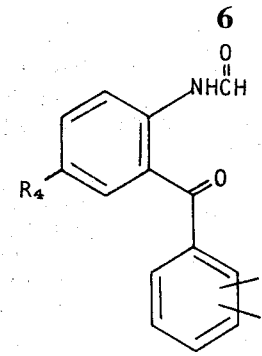

(b)

↓ hydrazine in ethanol

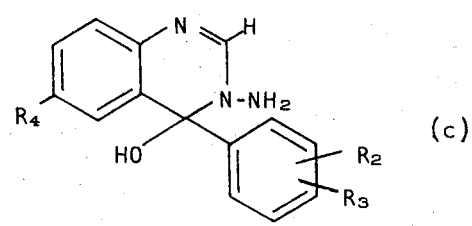

(c)

↓

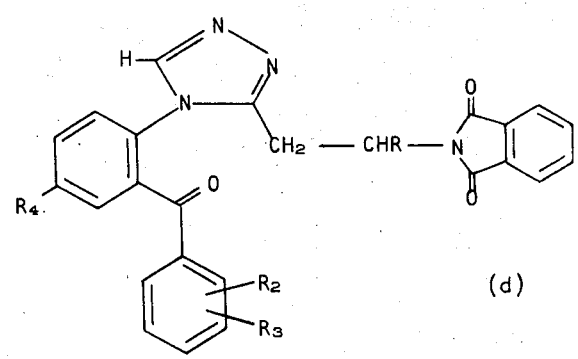

(d)

↓

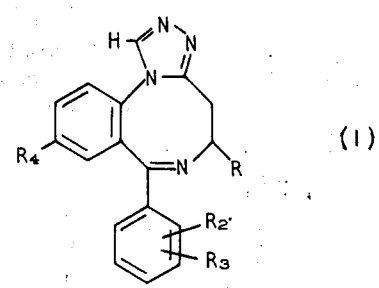

(1)

wherein R is hydrogen or alkyl of 1 to 3 carbon atoms inclusive; wherein $R_2$ is hydrogen, chloro, or fluoro; wherein $R_3$ is hydrogen or fluoro with the proviso that $R_3$ is not fluoro if $R_2$ is chloro; wherein $R_4$ is hydrogen, chloro, bromo, fluoro, nitro, or trifluoromethyl.

Compounds of formula (a) including those with the above mentioned substituents are well described in the literature. The process to synthesize such compounds to give the known compounds of formula (c) (through the intermediate compound of formula (b) is specifically described by Derieg, et al., J. Org. Chem. 36, 783 (1971).

The conversion of compounds of formula (c) to the present starting product I is achieved by the following preparations:

PREPARATION 1

5-Chloro-2-[3-(2-phthalimidoethyl)-4H-1,2,4-triazol-4-yl]benzophenone

A stirred mixture of 3-amino-6-chloro-3,4-dihydro-4-hydroxy-4-phenylquinazoline (2.74 g. 0.01 mole) in dry tetrahydrofuran (150 ml.) is cooled in an ice bath, under nitrogen, and treated with dry pyridine (1.77 ml., 0.022 mole). This mixture is then treated dropwise, during 1 hour with a solution of β-phthalimidopropionyl chloride (5.23 g., 0.022 mole) in tetrahydrofuran (25 ml.). The mixture is kept in the ice bath for 1 hour and at ambient temperature for 4 hours. It is then poured into cold, dilute aqueous sodium bicarbonate and extracted with chloroform. The extract is washed with brine, dried over anhydrous sodium sulfate and concentrated in vacuo. The residue is mixed with toluene (165 ml.), treated with trifluoroacetic acid (0.732 ml.) and warmed, under nitrogen at 100°–110° C. for 1.5 hours. The mixture is concentrated in vacuo and the residue mixed with cold water and extracted with chloroform. The extract is washed with brine, dried over anhydrous sodium sulfate and concentrated. The residue is chromatographed on silica gel (300 g) with 1.5% methanol-98.5% chloroform. The product thus obtained is crystallized to give 5-chloro-2-[3-(2-phthalimidoethyl)-4H-1,2,4-triazol-4-yl]benzophenone.

PREPARATION 2

9-Chloro-4,5-dihydro-7-phenyl-s-triazolo[4,3-a][1,4]benzodiazocine

A stirred solution of 5-chloro-2-[3-(2-phthalimidoethyl)-4H-1,2,4-triazol-4-yl]benzophenone (18.7 g., 0.041 mole) in absolute ethanol (250 ml.) is treated with hydrazine hydrate (4.15 g., 0.0829 mole) and warmed to 70° C. for 1.5 hours under nitrogen. The resulting precipitate which forms is filtered and washed with ethanol and methylene chloride and discarded. The filtrate from above, combined with the washings, is concentrated in vacuo and the residue mixed with water and extracted with methylene chloride. The extract is washed with brine, dried over anhydrous sodium sulfate and concentrated in vacuo. The resulting oil is crystallized from ethyl acetate to give 9-chloro-4,5-dihydro-7-phenyl-s-triazolo[4,3-a][1,5]benzodiazocine.

PREPARATION 3

2′,5-Dichloro-2-[3-(2-phthalimidoethyl)-4H-1,2,4-triazol-4-yl]benzophenone

A. N-[6-chloro-4-hydroxy-4-(o-chlorophenyl)-3(4H)-quinazolinyl]-1,3-dioxo-2-isoindolinepropionamide To an ice cold solution of β-phthalimidopropionic acid (2.41 g., 0.011 mole) in dry tetrahydrofuran (20 ml.) is added 1,1′-carbonyldiimidazole (1.94 g., 0.011 mole) under nitrogen. The ice bath is removed and the reaction stirred for 1 hours before the bath is replaced and 3-amino-6-chloro-3,4-dihydro-4-hydroxy-4-(o-chlorophenyl)-quinazoline (3.22 g., 0.01 mole) in tetrahydrofuran (25 ml.) is added. The reaction is stirred for 18 hours at ambient temperature before the reaction is concentrated in vacuo. The residue is mixed with water, neutralized with sodium bicarbonate and extracted with methylene chloride. The extract is washed with brine, dried over anhydrous sodium sulfate and concentrated in vacuo to give N-[6-chloro-4-hydroxy-4-(o-chlorophenyl)-3(4H)-quinazolinyl]-1,3-dioxo-2-isoindolinepropionamide.

B. 2′,5-Dichloro-2-[3-(2-phthalimidoethyl)-4H-1,2,4-triazol-4-yl]benzophenone

The product of Preparation 3A above is dissolved in acetic acid (50 ml.) and refluxed for 1 hour under nitrogen. The reaction is concentrated in vacuo and the residue mixed with water and methylene chloride. The solution is neutralized with sodium bicarbonate and the methylene chloride separated, washed with water, dried over anhydrous sodium sulfate and concentrated in vacuo. The resulting oil is chromatographed on silica gel (410 g.) with 2½% methanol-97½% chloroform. The product thus obtained is crystallized from ethyl acetate-Skellysolve B (hexanes) to give 2′,5-dichloro-2-[3-(2-phthalimidoethyl)-4H-1,2,4-triazol-4-y]benzophenone.

PREPARATION 4

9-Chloro-7-(o-chlorophenyl)-4,5-dihydro-s-triazolo[4,3-a][1,5]benzodiazocine

A stirred mixture of 2′,5-dichloro-2-[3-(2-phthalimidoethyl)-4H-1,2,4-triazol-4-yl]benzophenone (4.91 g., 0.01 mole) and absolute ethanol (60 ml.) is treated with hydrazine hydrate (0.751 g., 0.015 mole) and warmed in an oil bath at 73° C. for 90 minutes. The cooled mixture is mixed with water and extracted with chloroform. The extract is washed with brine, dried over anhydrous sodium slfate and concentrated. The residue is chromatographed on silica gel (250 g.) with 2% methanol-98% chloroform. The product thus obtained is crystallized from ethyl acetate to give 9-chloro-7-(o-chlorophenyl)-4,5-dihydro-s-triazolo[4,3-a][1,5]benzodiazocine.

PREPARATION 5

2′-Chloro-2-[3-(2-phthalimidoethyl)-4H-1,2,4-triazol-4-yl]benzophenone

A. 1,3-dioxo-2-isoindolinepropionic acid, [[N-[2-(o-chlorobenzoyl)phenyl]-1,3-dioxo-2-isoindolinepropionamido]methylene]hydrazide A stirred mixture of 3-amino-4-(o-chlorophenyl)-3,4-dihydro- 4-hydroxyquinazoline (2.74 g., 0.01 mole) in dry tetrahydrofuran (150 ml.) is cooled in an ice bath, under nitrogen, and treated with dry pyridine (1.77 ml., 0.022 mole). This mixture is then treated, dropwise, during 1 hour, with a solution of β-phthalimidopropionyl chloride (5.23 g., 0.022 mole) in tetrahydrofuran. The mixture is kept in the ice bath for an additional hour and at ambient temperature for 4 hours. It is then poured into cold aqueous sodium bicarbonate and extracted with chloroform. The chloroform extract is washed with brine, dried over anhydrous sodium sulfate and concentrated to give 1,3-dioxo-2-isoindolinepropionic acid, [[N-[2-(o-chlorobenzoyl)phenyl]-1,3-dioxo-2-isoindolinepropionamido]methylene]hydrazide.

B. 2'-Chloro-2-[3-(2-phthalimidoethyl)-4H-1,2,4-triazol-4-yl]benzophenone

The 1,3-dioxo-2-isoindolinepropionic acid, [[N-[2-(o-chlorobenzoyl)phenyl]-1,3-dioxo-2-isoindolinepropionamido]methylene]hydrazide from Preparation 5A is mixed with toluene (165 ml.), treated with trifluoroacetic acid (0.732 ml.) and warmed, under nitrogen, at 100°–110° C. for 1.5 hours. The mixture is concentrated in vacuo and the residue is mixed with cold, dilute sodium bicarbonate and extracted with chloroform. The extract is washed with brine, dried over anhydrous sodium sulfate and concentrated. The residue is chromatographed on silica gel (200 g.) with 2% methanol-98% chloroform. The product thus obtained is crystallized to give 2'-chloro-2-[3-(2-phthalimidoethyl)-4H-1,2,4-triazol-4-yl]benzophenone.

In the manner shown in Preparation 2, 2'-chloro-2-[3-(2-phthalimidoethyl)-4H-1,2,4-triazol-4-y]benzophenone is converted to 4,5-dihydro-7-(o-chlorophenyl)-s-triazolo-[4,3-a][1,5]benzodiazocine.

In the same manner given in the prior Preparations other 4,5-dihydro-7-phenyl-s-triazolo[4,3-a][1,5]benzodiazocines are obtained. Representative compounds thus obtained include:
9-bromo-4,5-dihydro-7-phenyl-s-triazolo[4,3-a][1,5]benzodiazocine;
9-nitro-4,5-dihydro-7-phenyl-s-triazolo[4,3-a][1,5]benzodiazocine;
9-fluoro-4,5-dihydro-7-phenyl-s-triazolo[4,3-a][1,5]benzodiazocine;
9-trifluoromethyl)-4,5-dihydro-7-phenyl-s-triazolo[4,3-a][1,5]benzodiazocine;
9-bromo-4,5-dihydro-7-(o-chlorophenyl)-s-triazolo[4,3-a][1,5]benzodiazocine;
9-nitro-4,5-dihydro-7-(o-chlorophenyl)-s-triazolo[4,3-a][1,5]benzodiazocine;
9-fluoro-4,5-dihydro-7-(o-chlorophenyl)-s-triazolo[4,3-a][1,5]benzodiazocine; 9-(trifluoromethyl)-4,5-dihydro-7-(o-chlorophenyl)-s-triazolo[4,3-a][1,5]benzodiazocine;
9-chloro-4,5-dihydro-7-(2,6-difluorophenyl)-s-triazolo[4,3-a][1,5]benzodiazocine;
9-(trifluoromethyl)-4,5-dihydro-7-(o-fluorophenyl)-s-triazolo[4,3-a][1,5]benzodiazocine;
9-nitro-4,5-dihydro-7-(p-fluorophenyl)-s-triazolo[4,3-a][1,5]benzodiazocine;
9-nitro-4,5-dihydro-7-(m-chlorophenyl)-s-triazolo[4,3-a][1,5]benzodiazocine;
9-chloro-4,5-dihydro-7-(o-fluorophenyl)-s-triazolo[4,3-a][1,5]benzodiazocine;
9-fluoro-4,5-dihydro-7-(2,6-difluorophenyl)-s-triazolo[4,3-a][1,5]benzodiazocine;
9-chloro-4,5-dihydro-5-methyl-7-(o-fluorophenyl)-s-triazolo[4,3-a][1,5]benzodiazocine;
9-fluoro-4,5-dihydro-7-(o-fluorophenyl)-s-triazolo[4,3-a][1,5]benzodiazocine;
9-chloro-4,5-dihydro-5-ethyl-7-phenyl-s-triazolo[4,3-a][1,5]benzodiazocine;
9-(trifluoromethyl)-4,5-dihydro-5-propyl-7-phenyl-s-triazolo[4,3-a][1,5]benzodiazocine;
9-chloro-4,5-dihydro-5-methyl-7-(o-chlorophenyl)-s-triazolo[4,3-a][1,5]benzodiazocine; and the like.

EXAMPLE 1

1-[2-(Dimethylamino)ethyl]-8-chloro-6-phenyl-4H-s-triazolo[4,3-a][1,4]benzodiazepine and its dicyclohexanesulfamate A. 5-Chloro-2-[3-[2-(dimethylamino)ethyl]-5-(hydroxymethyl)-4H-1,2,4-triazol-4-yl]benzophenone A stirred solution of 9-chloro-4,5-dihydro-7-phenyl-s-triazolo[4,3-a][1,5]benzodiazocine (3.09 g., 0.01 mole), 37% aqueous formaldehyde (7.3 g., 0.09 mole) and 88% formic acid (7.8 g., 0.15 mole) is refluxed, under nitrogen for 18 hours. The resulting mixture is poured into water, neutralized with sodium hydroxide and extracted with chloroform. The extract is washed (brine), dried over anhydrous sodium sulfate and concentrated. The residue is chromatographed on silica gel (200 g.) with methanol. The product thus obtained is crystallized from ethyl acetate-Skellysolve B hexanes to give 5-chloro-2-[3-[2-(dimethylamino)ethyl]-5-(hydroxymethyl)-4H-1,2,4-triazol-4-yl]benzophenone which is used in the next step.

B. 5-Chloro-2-[3-[2-(dimethylamino)ethyl]-5-(phthallmidomethyl)-4H-1,2,4-triazol-4-yl]benzophenone A stirred mixture of 5-chloro-2-[3-[2-(dimethylamino)ethyl]-5-(hydroxymethyl)-4H-1,2,4-triazol-4-yl]benzophenone (3.85 g., 0.01 mole), phthalimide (1.62 g., 0.011 mole), triphenylphosphine (2.88 g., 0.011 mole) and dry tetrahydrofuran (100 ml.) under nitrogen is treated with diethylazodicarboxylate (1.92 g., 0.011 mole) and stirred at ambient temperature for 20 hours. The mixture is concentrated in vacuo and the residue is chromatographed on silica gel (200 g.) with methanol. The product thus obtained is crystallized from ethyl acetate to give 5-chloro-2-[3-[2-(dimethylamino)ethyl]-5-(phthalimidomethyl)-4H-1,2,4-triazolo-4-yl]benzophenone.

C. 1-[2-(Dimethylamino)ethyl]-8-chloro-6-phenyl-4H-s-triazolo[4,3-a][1,4]benzodiazepine dicyclohexanesulfamate A stirred mixture of 5-chloro-2-[3-[2-(dimethylamino)ethyl-5-(phthalimidomethyl)-4H-1,2,4-triazol-4-yl]benzophenone (5.14 g., 0.01 mole), hydrazine hydrate (0.751 g., 0.015 mole) and absolute ethanol (60 ml.) is warmed in an oil bath, under nitrogen, at 70° C. for 3 hours. The resulting mixture is cooled in an ice bath, and the solid is removed by filtration and washed with ethanol and chloroform. The filtrate is concentrated and the resulting residue mixed with water and extracted with chloroform. The extract is washed with brine, dried over anhydrous sodium sulfate and concentrated. The residue is chromatographed on silica gel (200 g.,) and eluted first with 10% methanol-90% chloroform and finally with methanol. The product, 1-[2-(dimethylamino)ethyl]-8-chloro-6-phenyl-4H-s-triazolo[4,3-a][1,4]benzodiazepine, is obtained as an oil which is dissolved in ethyl acetate and treated with an equal weight of cyclohexanesulfamic acid. The resulting salt is crystallized from ethanol-ethyl acetate to give 1-[2-(dimethylamino)ethyl]-8-chloro-6- phenyl-4H-s-triazolo[4,3-a][1,4]benzodiazepine dicyclohexanesulfamate of melting point 132°–139° C.

EXAMPLE 2

1-[2-(dimethylamino)ethyl]-8-chloro-6-(o-chlorophenyl)-4H-s-triazolo[4,3-a][1,4]benzodiazepine A. 2',5-Dichloro-2-[3-[2-(dimethylamino)ethyl]-5-hydroxymethyl)-4H-1,2,4-triazol-4-yl]benzophenone In the manner given in Example 1A, 9-chloro-4,5-dihydro-7-(o-chlorophenyl)-s-triazolo[4,3-a][1,5]benzodiazocine is treated with formalin in formic acid solution to give 2',5-dichloro-2-[3-[2-(dimethylamino)ethyl]-5-(hydroxymethyl)-4H-1,2,4-triazol-4-yl]benzophenone.

B. 2',5-Dichloro-2-[3-[2-(dimethylamino)ethyl[-5-(phthalimidomethyl)-4H-1,2,4-triazol-4-yl]benzophenone In the manner given in Example 1B, 2',5-dichloro-2-[3-[2-(dimethylamino)ethyl]-5-(hydroxymethyl)-4H-1,2,4-triazol-4-yl]benzophenone in 1,2-dimethoxyethane is treated with phthalimide, triphenylphosphine and diethyl azodicarboxylate to give 2',5-dichloro-2-[3-[2-(dimethylamino)ethyl]-5-(phthalimidomethyl)-4H-1,2,4,-triazol-4-yl]benzophenone.

C. 1-[2-(Dimethylamino)ethyl]-8-chloro-6-(o-chlorophenyl)-4H-s-triazolo[4,3-a][1,4]benzodiazepine and its hydrochloride In the manner given in Example 1C, 2',5-dichloro-2-[3-[2-(dimethylamino)ethyl]-5-(phthalimidomethyl)-4H-1,2,4-triazol-4-yl]benzophenone in ethanol is refluxed with hydrazine to give 1-[2-(dimethylamino)ethyl]-8-chloro-6-(o-chlorophenyl)-4H-s-triazolo[4,3-a][1,4]benzodiazepine of melting point 150°–153° C.

EXAMPLE 3

1-[2-(Dimethylamino)ethyl]-8-nitro-6-(o-chlorophenyl)-4H-s-triazolo[4,3-a][1,4]benzodiazepine and its hydrochloride A. 2'-Chloro-5-nitro-2-[3-[2-(dimethylamino)ethyl]-5-(hydroxymethyl)-4H-1,2,4-triazol-4-yl]benzophenone In the manner given in Example 1A, 9-nitro-4,5-dihydro-7-(o-chlorophenyl)-s-triazolo[4,3-a][1,5]benzodiazocine is treated with formalin in formic acid solution to give 2'-chloro-5-nitro2-[3-[2-(dimethylamino)ethyl]-5-(hydroxymethyl)-4H-1,2,4-triazol-4-yl]benzophenone.

B. 2'-Chloro-5-nitro-2-[3-[2-(dimethylamino)ethyl]-5-(phthalimidomethyl)-4H-1,2,4-triazol-4-yl]benzophenone In the manner given in Example 1B, 2'-chloro-5-nitro-2-[3-[2-(dimethylamino)ethyl]-5-(hydroxymethyl)-4H-1,2,4-triazol-4-yl]benzophenone in 1,2-dimethoxyethane is treated with phthalimide, triphenylphosphine and diethyl azodicarboxylate to give 2'-chloro-5-nitro-2-[3-[2-(dimethylamino)ethyl]-5-(phthalimidomethyl)-4H-1,2,4-triazol-4-yl]benzophenone.

C. 1-[2-(Dimethylamino)ethyl]-8-nitro-6-(o-chlorophenyl-4H-s-triazolo[4,3-a][1,4]benzodiazepine and its hydrochloride In the manner given in Example 1C, 2'-chloro-5-nitro-2-[3-[2-(dimethylamino)ethyl]-5-(phthalimidomethyl)-4H-1,2,4-triazol-4-yl]benzophenone in ethanol is refluxed with hydrazine to give 1-[2-(dimethylamino)ethyl]-8-nitro-6-(o-chlorophenyl)-4H-s-triazolo[4,3-a][1,4]benzodiazepine. This compound is converted to its hydrochloride by treating it with ethereal hydrogen chloride.

EXAMPLE 4

1-[2-(Dimethylamino)ethyl]-8-fluoro-6-phenyl-4H-s-triazolo[4,3-a][1,4] benzodiazepine and its hydrobromide A. 5-Fluoro-2-[3-[2-(dimethylamino)ethyl]-5-(hydroxymethyl)-4H-1,2,4-triazol-4-yl]benzophenone In the manner given in Example 1A, 9-fluoro-4,5-dihydro-7-phenyl-s-triazolo[4,3-a][1,5]benzodiazocine is treated with formalin in formic acid solution to give 5-fluoro-2-[3-[2-(dimethylamino)ethyl]-5-(hydroxymethyl)-4H-1,2,4-triazol-4-yl]benzophenone.

B. 5-Fluoro-2-[3-[2-(dimethylamino)ethyl]-5-(phthalimidomethyl)-4H-1,2,4-triazol-4-yl]benzophenone In the manner given in Example 1B, 5-fluoro-2-[3-[2-(dimethylamino)ethyl]-5-(hydroxymethyl)-4H-1,2,4-triazol-4-yl]benzophenone in 1,2-dimethoxyethane is treated with phthalimide, triphenylphosphine and diethyl azodicarboxylate to give 5-fluoro-2-[3-[2-(dimethylamino)-ethyl]-5-(phthalimidomethyl)-4H-1,2,4-triazol-4-yl]benzophenone.

C. 1-[2-(Dimethylamino)ethyl]-8-fluoro-6-phenyl-4H-s-triazolo[4,3-a][1,4]benzodiazepine and its hydrobromide In the manner given in Example 1C, 5-fluoro-2-[3-[2-(dimethylamino)ethyl]-5-(phthalimidomethyl)-4H-1,2,4-triazol-4-yl]benzophenone in ethanol is refluxed with hydrazine hydrate to give 1-[2-(dimethylamino)ethyl]-8-fluoro-6-phenyl-4H-s-triazolo[4,3-a][1,4]benzodiazepine. This compound is converted to its hydrobromide by treating it with hydrogen bromide gas in ether.

EXAMPLE 5

1-[2-(dimethylamino)ethyl]-6-(o-chlorophenyl)-4H-s-triazolo[4,3-a][1,4]benzodiazepine and its methanesulfamate A. 2'-Chloro-2-[3-[2-(dimethylamino)ethyl]-5-(hydroxymethyl)-4H-1,2,4-triazol-4-yl]benzophenone In the manner given in Example 1A, 4,5-dihydro-7-(o-chlorophenyl)-s-triazolo[4,3-a][1,5]benzodiazocine is treated with formalin in formic acid solution to give 2'-chloro-2-[3-[2-(dimethylamino)ethyl]-5-(hydroxymethyl)-4H-1,2,4-triazol-4-yl]benzophenone.

B. 2'-Chloro-2-[3-[2-(dimethylamino)ethyl]-5-(phthalimidomethyl)-4H-1,2,4-triazol-4-yl]benzophenone In the manner given in Example 1B, 2'-chloro-2-[3-[2-(dimethylamino)ethyl]-5-(hydroxymethyl)-4H-1,2,4-triazol-4-yl]benzophenone in tetrahydrofuran is treated with phthalimide, triphenylphosphine and diethylazodicarboxylate to give 2'-chloro-2-[3-[2-(dimethylamino)-ethyl]-5-(phthalimidomethyl)-4H-1,2,4-triazol-4-yl]benzophenone.

C. 1-[2-(dimethylamino)ethyl]-6-(o-chlorphenyl)-4H-s-triazolo[4,3-a][1,4]benzodiazepine and its methanesulfamate In the manner given in Example 1C, 2'-chloro-2-[3-[2-(dimethylamino)ethyl]-5-(phthalimidomethyl)-4H-1,2,4-triazol-4-yl]benzophenone in ethanol is refluxed with hydrazine hydrate to give 1-[2-(dimethylamino)ethyl]-6-(o-chlorophenyl)-4H-s-triazolo-[4,3-a][1,4]benzodiazepine. Its methanesulfamate is obtained by treatment with methanesulfamic acid in ether.

EXAMPLE 6

1-[2-(dimethylamino)ethyl]-8-chloro-6-(2,6-difluorophenyl)-4H-s-triazolo]4,3-a][1,4]benzodiazepine and its hydrochloride A. 5-Chloro-2',6'-difluoro-2-[3-[2-(dimethylamino)ethyl]-5-(hydroxymethyl)-4H-1,2,4-triazol-4-yl]benzophenone In the manner given in Example 1A, 9-chloro-4,5-dihydro-7-(2,6-difluorophenyl)-s-triazolo[4,3-a][1,5]-benzodiazocine is treated with formalin in formic acid solution to give 5-chloro-2',6'-difluoro-2-[3-[2-(dimethylamino)ethyl]-5-(hydroxymethyl)-4H-1,2,4-triazol-4-yl]benzophenone.

B. 5-Chloro-2',6'-difluoro-2-[3-[2-(dimethylamino)ethyl]-5-(phthalimidomethyl)-4H-1,2,4-triazol-4-yl]benzophenone In the manner given in Example 1B, 5-chloro-2',6'-difluoro-2-[3-[2-(dimethylamino)ethyl]-5-(hydroxymethyl)-4H-1,2,4-triazol-4-yl]benzophenone in methylene chloride is treated with phthalimide, triphenylphosphine and diethyl azodicarboxylate to give 5-chloro-2',6'-difluoro-2-[3-[2-(dimethylamino)ethyl]-5-(phthalimidomethyl)-4H-1,2,4-triazol-4-yl]benzophenone.

C. 1-[2-(dimethylamino)ethyl]-8-chloro-6-(2',6'-difluorophenyl)-4H-s-triazolo[4,3-][1,4]benzodiazepine and its hydrochloride In the manner given in Example 1C, 5-chloro-2',6'-difluoro-2-[3-[2-(dimethylamino)ethyl]-5-(phthalimidomethyl)-4H-1,2,4-triazol-4-yl]benzophenone in ethanol is refluxed with hydrazine hydrate to give 1-[2-(dimethylamino)ethyl]-8-chloro-6-(2,6-difluorophenyl)-4H-s-triazolo-[4,3-a][1,4]benzodiazepine. This compound is converted to its hydrochloride by treating it with ethereal hydrogen chloride.

EXAMPLE 7

1-[2-(dimethylamino)ethyl]-8-fluoro-6-(o-chlorophenyl)-4H-s-triazolo[4,3-a][1,4]benzodiazepine A. 2'-Chloro-5-fluoro-2-[3-[2-(dimethylamino)ethyl]-5-(hydroxymethyl)-4H-1,2,4-triazol-4-yl]benzophenone In the manner given in Example 1A, 9-fluoro-4,5-dihydro-7-(o-chlorophenyl)-s-triazolo[4,3-a][1,5]benzodiazocine is treated with formalin in formic acid solution to give 5-fluoro-2'-chloro-2-[3-[2-(dimethylamino)ethyl]-5-(hydroxymethyl)-4H-1,2,4-triazol-4-yl]benzophenone.

B. 2'-Chloro-5-fluoro-2-[3-[2-(dimethylamino)ethyl]-5-(phthalimidomethyl)-4H-1,2,4-triazol-4-yl]benzophenone In the manner given in Example 1B, 2'-chloro-5-fluoro-2-[3-[2-(dimethylamino)ethyl]-5-(hydroxymethyl)-4H-1,2,4-triazol-4-yl]benzophenone in tetrahydrofuran is treated with phthalimide, triphenylphosphine and diethyl azodicarboxylate to give 2'-chloro-5-fluoro-2-[3-[2-(dimethylamino)ethyl]-5-(phthalimidomethyl)-4H-1,2,4-triazol- 4-yl]benzophenone.

C. 1-[2-(Dimethylamino)ethyl]-8-fluoro-6-(o-chlorophenyl)-4H-s-triazolo[4,3-a][1,4]benzodiazepine In the manner given in Example 1C, 2'-chloro-5-fluoro-2-[3-[2-(dimethylamino)ethyl]-5-(phthalimidomethyl)-4H-1,2,4-triazol-4-yl]benzophenone in ethanol is refluxed with hydrazine to give 1-[2-(dimethylamino)ethyl]-8-fluoro-6-(o-chlorophenyl)-4H-s-triazolo[4,3-a][1,4]benzodiazepine.

EXAMPLE 8

1-[2-(Dimethylamino)ethyl]-8-(trifluoromethyl)-6-(o-chlorophenyl)-4H-s-triazolo[4,3-a][1,4]benzodiazepine and its hydrochloride A. 5-Trifluoromethyl)-2'-chloro-2-[3-[2-(dimethylamino)ethyl]-5-(hydroxymethyl)-4H-1,2,4-triazol-4-yl]-benzophenone In the manner given in Example 1A, 9-(trifluoromethyl)-4,5-dihydro-7-(o-chlorophenyl)-s-triazolo[4,3-a]-(1,5]benzodiazocine is treated with formalin in formic acid solution to give 5-(trifluoromethyl)-2'-chloro-2-[3-[2-(dimethylamino)ethyl]-5-(hydroxymethyl)14H-1,2,4-triazol-4-yl]benzophenone.

B. 5-(Trifluoromethyl)-2'-chloro-2-[3-[2-(dimethylamino)ethyl]-5-(phthalimidomethyl)-4H-1,2,4-triazol-4-yl]-benzophenone In the manner given in Example 1B, 5-(trifluoromethyl)-2'-chloro-2-[3-[2-(dimethylamino)ethyl]-5-(hydroxymethyl)-4H-1,2,4-triazol-4-yl]benzophenone in 1,2-dimethoxyethane is treated with phthalimide, triphenylphosphine and diethyl azodicarboxylate to give 5-(trifluoromethyl)-2'-chloro-2-[3-[2-(dimethylamino)ethyl]-5-(phthalimidomethyl)-4H-1,2,4-triazol-4-yl]benzophenone.

C. 1-[2-(Dimethylamino)ethyl]-8-(trifluoromethyl)-6-(o-chlorophenyl)-4H-s-triazolo[4,3-a][1,4]benzodiazepine and its hydrochloride In the manner given in Example 1C, 5-(trifluoromethyl)-2'-chloro-2-[3-[2-(dimethylamino)ethyl-5-(phthalimidomethyl)-4H-1,2,4-triazol-4-yl]benzophenone in ethanol is refluxed with hydrazine to give 1-[2-(dimethylamino)-ethyl]-8-(trifluoromethyl)-6-(o-chlorophenyl)-4H-s-triazolo-[4,3-a][1,4]benzodiazepine. This compound is converted to its hydrochloride by treating it with hydrogen chloride in ether.

In the manner given in Example 1A other 2-[3-[2-(dimethylamino)ethyl]-5-(hydroxymethyl)-4H-1,2,4-triazol-4-yl]benzophenones (II) can be synthesized such as:

5-chloro-2'-fluoro-2-[3-[2-(dimethylamino)ethyl]-5-(hydroxymethyl)-4H-1,2,4-triazol-4-yl]benzophenone;

2',5-difluoro-2-[3-[2-(dimethylamino)ethyl]-5-(hydroxymethyl)-4H-1,2,4-triazol-4-yl]benzophenone;

5-chloro-3'-fluoro-2-[3-[2-(dimethylamino)ethyl]-5-(hydroxymethyl)-4H-1,2,4-triazol-4-yl]benzophenone;

3',5-dichloro-2-[3-[2-(dimethylamino)ethyl]-5-(hydroxymethyl)-4H-1,2,4-triazol-4-yl]benzophenone;

5-bromo-2'-chloro-2-[3-[2-(dimethylamino)ethyl]-5-(hydroxymethyl)-4H-1,2,4-triazol-4-yl]benzophenone;

5-bromo-2-[3-[2-(dimethylamino)ethyl]-5-(hydroxymethyl)-4H-1,2,4-triazol-4-yl]benzophenone;

5-nitro-2-[3-[2-(dimethylamino)ethyl]-5-(hydroxymethyl)-4H-1,2,4-triazol-4-yl]benzophenone;

5-nitro-3'-chloro-2-[3-[2-(dimethylamino)ethyl[-5-(hydroxymethyl)-4H-1,2,4-triazol-4-yl]benzophenone;

2'-fluoro-2-[3-[2-(dimethylamino)ethyl]-5-(hydroxymethyl)-4H-1,2,4-triazol-4-yl]benzophenone;

5-nitro-4'-chloro-2-[3-[2-(dimethylamino)ethyl]-5-(hydroxymethyl)-4H-1,2,4-triazol-4-yl]benzophenone;

5-(trifluoromethyl)-2-[3-[2-(dimethylamino)ethyl]-5-(hydroxymethyl)-4H-1,2,4-triazol-4-yl]benzophenone;

5-chloro-2'-fluoro-2-[3-[2-(dimethylamino)propyl]-5-(hydroxymethyl)-4H-1,2,4-triazol-4-yl]benzophenone;

5-chloro-2-[3-[2-(dimethylamino)butyl]-5-(hydroxymethyl)-4H-1,2,4-triazol-4-yl]benzophenone;

5-(trifluoromethyl)-2-[3-[2-(dimethylamino)pentyl]-5-(hydroxymethyl)-4H-1,2,4-triazol-4-yl]benzophenone;

2',5-dichloro-2-[3-[2-(dimethylamino)propyl]-5-(hydroxymethyl)-4H-1,2,4-triazol-4-yl]benzophenone;

and the like.

In the same manner given in Example 1B, other 2-[3-[2-(dimethylamino)ethyl]-5-(phthalimidomethyl)-4H-1,2,4-triazol-4-yl]benzophenones III can be synthesized. Representative compounds thus obtained include;

5-chloro-2'-fluoro-2-[3-[2-(dimethylamino)ethyl]-5-(phthalimidomethyl)-4H-1,2,4-triazol-4-yl]benzophenone;

2',5-difluoro-2-[3-[2-(dimethylamino)ethyl]-5-(phthalimidomethyl)-4H-1,2,4-triazol-4-yl]benzophenone;

5-chloro-3'-fluoro-2-[3-[2-(dimethylamino)ethyl]-5-(phthalimidomethyl)-4H-1,2,4-triazol-4-yl]benzophenone;

3',5-dichloro-2-[3-[2-(dimethylamino)ethyl]-5-(phthalimidomethyl)-4H-1,2 4-triazol-4-yl]benzophenone;

5-bromo-2'-chloro-2-[3-[2-(dimethylamino)ethyl]-5-(phthalimidomethyl)-4H-1,2,4-triazol-4-yl]benzophenone;

5-bromo-2-[3-[2-(dimethylamino)ethyl]-5-(phthalimidoethyl)-4H-1,2,4-triazol-4-yl]benzophenone;

5-nitro-2-[3-[2-(dimethylamino)ethyl]-5-(phthalimidomethyl)-4H-1,2,4-triazol-4-yl]benzophenone;

5-nitro-3'-chloro-2-[3-[2-(dimethylamino)ethyl]-5-(phthalimidomethyl)-4H-1,2,4-triazol-4-yl]benzophenone;

2'-fluoro-2-[3-[2-(dimethylamino)ethyl]-5-(phthalimidomethyl)-4H-1,2,4-triazol-4-yl]benzophenone;

5-nitro-4'-chloro-2-[3-[2-(dimethylamino)ethyl]-5-(phthalimidomethyl(-4H-1,2,4-triazol-4-yl]benzophenone;

5-(trifluoromethyl)-2-[3-[2-(dimethylamino)ethyl]-5-(phthalimidomethyl)-4H-1,2,4-triazol-4-yl]benzophenone;

5-chloro-2'-fluoro-2-[3-[2-(dimethylamino)propyl]-5-(phthalimidomethyl)-4H-1,2,4-triazol-4-yl]benzophenone;

5-chloro-2-[3-[2-(dimethylamino)butyl]-5-(phthalimidomethyl)-4H-1,2,4-triazol-4-yl]benzophenone;

5-(trifluoromethyl)-2-[3-[2-(dimethylamino)pentyl)]-5-(phthalimidomethyl)-4H-1,2,4-triazol-4-yl]benzophenone;

2',5-dichloro-2-[3-[2-(dimethylamino)propyl]-5-(phthalimidomethyl)-4H-1,2,4-triazol-4-yl]benzophenone;

and the like.

The compounds of formula II and III can be converted to their pharmaceutically acceptable acid addition salts by treatment with an acid such as hydrochloric, hydrobromic, sulfuric, cyclohexanesulfamic, methanesulfonic, toluenesulfonic, acetic, lactic, tartaric, and the like acids.

In the same manner given in Example 1C, other 1-[2-(dimethylamino)alkyl]-6-phenyl-4H-s-triazolo[4,3-][1,4]benzodiazepines of formula IV can be synthesized. Representative compounds thus obtained include:

8-chloro-1-[2-(dimethylamino)ethyl]-6-(o-fluorophenyl)-4H-s-triazolo[4,3-a][1,4]benzodiazepine;

8-fluoro-1-[2-(dimethylamino)ethyl]-6-(o-fluorophenyl)-4H-s-triazolo[4,3-a][1,4]benzodiazepine;

8-chloro-1-[2-(dimethylamino)ethyl]-6-(m-fluorophenyl)-4H-s-triazolo[4,3-a][1,4]benzodiazepine;

8-chloro-1-[2-(dimethylamino)ethyl]-6-(m-chlorophenyl)-4H-s-triazolo[4,3-a][1,4]benzodiazepine;

8-bromo-1-[2-(dimethylamino)ethyl]-6-(o-chlorophenyl)-4H-s-triazolo[4,3-a][1,4]benzodiazepine;

8-bromo-1-[2-(dimethylamino)ethyl]-6-phenyl-4H-s-triazolo[4,3-a][1,4]benzodiazepine;

8-nitro-1-[2-(dimethylamino)ethyl]-6-phenyl-4H-s-triazolo[4,3-a][1,4]benzodiazepine;

8-nitro-1-[2-(dimethylamino)ethyl]-6-(m-chlorophenyl)-4H-s-triazolo[4,3-a][1,4]benzodiazepine;

1-[2-(dimethylamino)ethyl]-6-(o-fluorophenyl)-4H-s-triazolo[4,3-a][1,4]benzodiazepine;

8-nitro-1-[2-(dimethylamino)ethyl]-6-(p-chlorophenyl)-4H-s-triazolo[4,3-a][1,4]benzodiazepine;

8-(trifluoromethyl)-1-[2-(dimethylamino)ethyl]-6-phenyl-4H-s-triazolo[4,3-a][1,4]benzodiazepine;

8-chloro-1-[2-(dimethylamino)propyl]-6-(o-fluorophenyl)-4H-s-triazolo[4,3-a][1,4]benzodiazepine;

8-chloro-1-[2-(dimethylamino)butyl]-6-phenyl-4H-s-triazolo[4,3-a][1,4]benzodiazepine;

8-(trifuloromethyl)-1-[2-(dimethylamino)pentyl]-6-phenyl-4H-s-triazolo[4,3-a][1,4]benzodiazepine;

8-chloro-1-[2-(dimethylamino)propyl]-6-(o-chlorophenyl)-4H-s-triazolo[4,3-a][1,4]benzodiazepine;

8-chloro-1-[2-(dimethylamino)propyl]-6-(2,4-difluorophenyl)-4H-s-triazolo[4,3-a][1,4]benzodiazepine;

and the like.

I claim:

1. A process for the preparation of a compound of the formula IV:

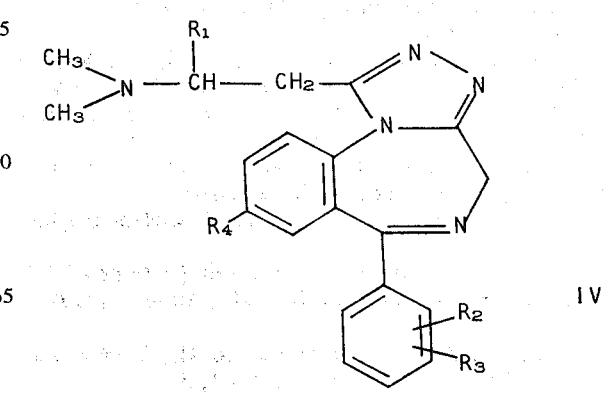

wherein $R_1$ is hydrogen or alkyl of 1 to 3 carbon atoms, inclusive; wherein $R_2$ is hydrogen, chloro, or fluoro; wherein $R_3$ is hydrogen, or fluoro with the proviso that $R_3$ is not fluoro if $R_2$ is chloro; and wherein $R_4$ is hydrogen, chloro, fluoro, bromo, nitro, and trifluoromethyl, which comprises the following steps:

1. treating a compound of the formula I:

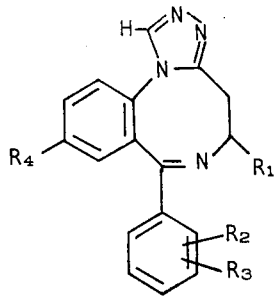

wherein $R_1$, $R_2$, $R_3$, and $R_4$ are defined as above, in formic acid solution with at least 3 molequivalents of aqueous formaldehyde per molequivalent of compound I, between 60° and 100° C., to obtain the corresponding compound II:

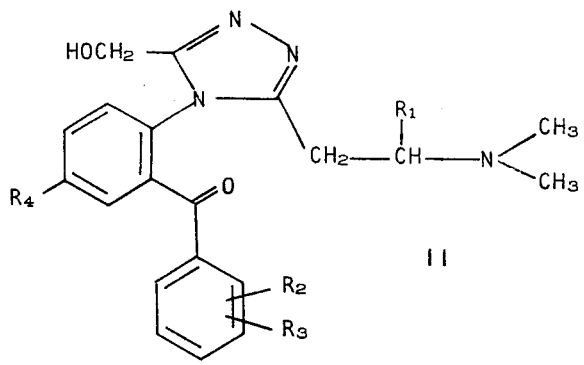

wherein $R_1$, $R_2$, $R_3$, and $R_4$ are defined as above;

2. treating compound II between 0° and 100° C., in an inert organic solvent, with phthalimide and triphenylphosphine and subsequently with diethyl azodicarboxylate to obtain the corresponding compound III:

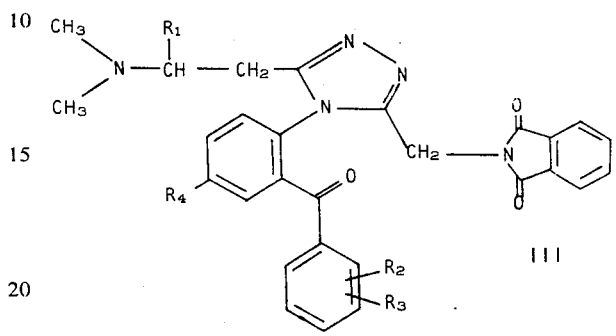

wherein $R_1$, $R_2$, $R_3$, and $R_4$ are defined as above; and 3. reacting compound III with a base to obtain the corresponding compound of formula IV above.

2. A process according to claim 1, wherein the starting compound I is 9-chloro-4,5-dihydro-7-phenyl-s-triazolo[4,3-a][1,5]benzodiazocine.

3. A process according to claim 1, wherein the starting compound I is 9-chloro-4,5-dihydro-7-(o-chlorophenyl)-s-triazolo[4,3-a][1,5]benzodiazocine.

4. The process according to claim 1, wherein the second step is performed at ambient temperatures between 18° to 30° C. and wherein the solvent is tetrahydrofuran or 1,2-dimethoxyethane.

5. The process of claim 1, wherein the base in step 3 to cyclize is hydrazine.

* * * * *